United States Patent [19]

Huemmer et al.

[11] 4,309,561
[45] Jan. 5, 1982

[54] PHOTOPOLYMERIZABLE ACRYLATE MONOMERS

[75] Inventors: Thomas F. Huemmer; Pallavoor R. Lakshmanan, both of Houston, Tex.

[73] Assignee: Gulf Oil Corporation, Pittsburgh, Pa.

[21] Appl. No.: 161,612

[22] Filed: Jun. 20, 1980

[51] Int. Cl.$^3$ .................. C07C 125/073; C08F 236/00
[52] U.S. Cl. ...................................... 560/26; 526/284; 560/115; 560/133; 560/134; 560/137; 560/158
[58] Field of Search .......................... 560/26, 115, 158

[56] References Cited

U.S. PATENT DOCUMENTS 4,078,015  3/1978  Leitheiser et al. .................. 560/26
4,104,144  8/1978  Weiss et al. ............................ 560/26

Primary Examiner—G. T. Breitenstein
Attorney, Agent, or Firm—Richard L. Kelly

[57] ABSTRACT

Acrylate monomers useful as a component of U.V. curable resin compositions and anaerobic adhesive compositions are provided and have the structure:

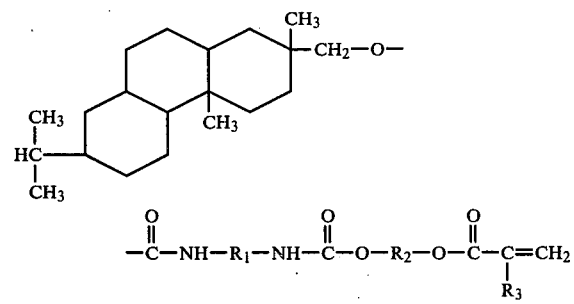

where the phenanthrene ring contains up to three (3) double bonds, where $R_1$ is a divalent radical, where $R_2$ is a divalent radical, and where $R_3$ is a hydrogen atom or an alkyl group.

10 Claims, No Drawings

PHOTOPOLYMERIZABLE ACRYLATE MONOMERS

BACKGROUND OF THE INVENTION

Photopolymerizable compositions and anaerobic adhesives have certain common characteristics. With each type of composition, the film-forming components comprise essentially the total composition, except for small quantities of photoinitiators, free radical polymerization initiators, plasticizers, and the like. The compositions do not contain solvents that need to be removed from the film or coatings.

While there are numerous photopolymerizable and anaerobic adhesive compositions available to the art, the art is constantly seeking monomeric materials for inclusion in such compositions which will improve their performance properties thereof. It is a principal object of the present invention to provide such improved monomeric materials.

CROSS REFERENCE TO RELATED APPLICATION

The novel monomers disclosed and claimed herein are included as an essential component in the anaerobic adhesive compositions disclosed and claimed in the applicants' copending application, Ser. No. 161,728, filed of even date herewith.

SUMMARY OF THE INVENTION

The applicants have invented certain copolymerizable acrylate monomers having the structure:

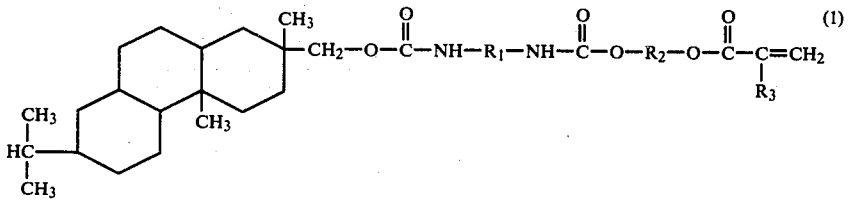

where the phenanthrene ring contains up to three (3) double bonds, where $R_1$ is a divalent radical, where $R_2$ is a divalent radical, and where $R_3$ is a hydrogen atom or an alkyl group.

The applicants also have invented certain photopolymerizable compositions containing such acrylate monomers as one component.

DETAILED DESCRIPTION OF THE INVENTION

In formula (1), the fused 14 carbon atom ring is a phenanthrene ring which may contain up to three double bonds. This segment of the acrylate monomer is derived from abietyl alcohol which is obtained by the reduction of abietic acid. In the course of the reduction, some of the double bonds in the ring may be hydrogenated.

In formula (1), $R_1$ is a divalent radical derived from a diisocyanate. Typically, the radical will be an arylene group such as a phenylene, tolylene, or a naphthylene group. The $R_1$ also can be an alkylene group such as a hexamethylene group.

In formula (1), $R_2$ likewise is a divalent radical. The simplest such radical is that shown below:

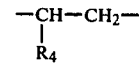

where $R_4$ is a hydrogen atom or an alkyl group. $R_2$ may be considerably more complex in structure as shown in formulae (2) and (3) below:

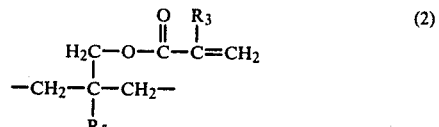

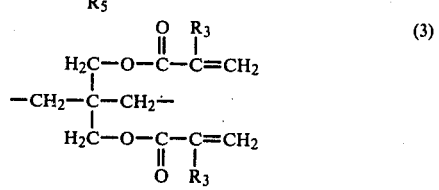

In formulae (2) and (3), $R_3$ is a hydrogen atom or an alkyl group. In formula (2), $R_5$ is an alkyl group.

In formula (1) $R_3$ is a hydrogen atom or an alkyl group.

The compounds of formula (1) are prepared by initially reacting abietyl alcohol with a diisocyanate compound such as toluene diisocyanate (TDI) in a 1/1 molar ratio. This reaction takes place under mild reaction conditions similar to those reported in the art for reacting diisocyanate compounds with other alcohols.

In the next step of the process, the intermediate compound of the above reaction is reacted in a 1/1 molar ratio with an acrylate-containing molecule having one hydroxyl group in the molecule that is free to react with the free isocyanate group of the first intermediate product. The simplest of these hydroxyl containing acrylate compounds is a hydroxyalkyl ester of acrylic acid, such as beta-hydroxypropyl acrylate (HPA). This second reaction proceeds smoothly under mild conditions similar to those employed in the first step of the process.

The abietyl alcohol employed in the preparation of the compounds of interest is that prepared by the reduction of abietic acid. A suitable material is sold under the trademark name Abitol and is identified as being a mixture of tetrahydroabietyl alcohol, dihydroabietyl alcohol, and dehydroabietyl alcohol.

Examples of suitable diisocyanates useful in the practice of the invention include toluene isocyanate, isophorone diisocyanate, hexamethylene diisocyanate, xylene diisocyanate, naphthalene diisocyanate, 3,3'-dimethyl-4,4'-diphenylmethane diisocyanate, durene diisocyanate, and lysine diisocyanate.

The hydroxy-containing acrylate compound employed in the synthesis is preferably a hydroxyalkyl acrylate, such as beta-hydroxyethyl acrylate, beta-hydroxyethyl methacrylate, beta-hydroxypropyl acrylate and the like. Where it is desired to incorporate two or more acrylate moieties into the compounds of the invention, the hydroxyl-containing acrylate compound employed in the synthesis can be a partial ester formed between a polyhydric alcohol containing three or more hydroxy groups and two or more acrylic or methacrylic acids. Typical intermediates of this type include pentaerythritol triacrylate and trimethylolpropane diacrylate.

When the compounds of formula (1) are prepared from trimethylol propane diacrylate, the $R_2$ group will have the structure shown in formula (2) above. When the compounds of formula (1) are prepared from pentaerythritol triacrylate, the $R_2$ group will have the structure shown in formula (3) above.

In preparing photopolymerizable compositions containing an acrylate monomer of the invention, the acrylate monomer will be blended with one or more additional polymerizable ethylenically unsaturated compound of the type employed in the photoinitiated coating compositions reported in the prior art. Typically, these materials will be complex esters or ethers containing two or more vinyl or allyl groups such as diallyl phthalate, diallyl maleate, diallyl fumarate, triallyl cyanaurate, triallyl phosphate, ethylene glycol dimethacrylate, glycerol trimethacrylate, pentaerythritol triacrylate, pentaerythritol tetraacrylate, trimethylolpropane triacrylate, methacrylic acid anhydride, and allyl ethers of polyhydroxy compounds such as ethylene glycol diallyl ether, pentaerythritol tetrallyl ether, and the like. Nonterminally unsaturated compounds such as diethyl fumarate can similarly be used. Many proprietary resins containing terminal allyl and acrylate groups are commercially available and can be employed. Many of these resins are modified urethane and epoxy resins. The novel acrylate monomer of the present invention should constitute at least 10 weight %, preferably 20–80 and more especially 20–40 weight % of the total monomers included in the photopolymerizable compositions.

In addition to the polymerizable monomers, the photopolymerizable compositions of the invention also will contain a photoinitiating compound. This can be any type commonly employed in the art, including the benzoin ethers, the benzophenone compounds, and the like. Frequently the compositions will contain an amine synergist such as methyl diethanolamine.

The anaerobic adhesive compositions of the invention will be essentially similar to the photopolymerizable compositions described above. The anaerobic adhesive will differ therefrom in not containing a photoinitiator and in including in the composition one or more free radical polymerization initiators such as cumene hydroperoxide or t-butyl hydroperoxide. Frequently minor components of other materials are included as cure accelerators such as dimethyltoluidine and saccharin.

The performance of photopolymerizable compositions containing acrylate monomers of the present invention were evaluated by curing coatings of such compositions. Most of the coatings were laid down on Leneta charts with a No. 4 wire rod. The coatings were cured in a QC Processor Model 1202 AN supplied by PPG Industries, Inc. The variables studied were line speed and the linear power density supplied by the mercury vapor lamps. The surface cure was determined by a simple touch test. Where the film surface was tack-free to the touch, the film cure then was measured by determining the number of rubs with an acetone impregnated cotton swab that were required to lift the film from the substrate.

The other tests performed on the cured films were conventional in the coating arts. By way of example, pencil hardness values were determined by ASTM D3363-74. An adhesion test consisted of applying Scotch brand cellophane tape to the coating, lifting the tape, and noting the percent (if any) of the coating lifted by the tape. Solvent resistance was measured by placing a segment of fine filter paper on the coating, saturating the paper with the solvent, placing a watch glass on the filter paper, and permitting the assembly to set for at least 16 hours at ambient temperature. The filter paper is removed and the film is examined visually to note any damage.

The following examples are set forth to illustrate more clearly the principle and practice of the invention to those skilled in the art. Where parts or percentages are set forth, they are parts and percentages by weight unless otherwise noted.

EXAMPLE 1

Part A

A round-bottom flask equipped with a dropping funnel, a stirrer, and a thermometer was charged with 216 grams (0.75 equivalent) of a technical grade abietyl alcohol sold under the trade name Abitol, 1.8 gram of dibutyl tin diacetate and 300 ml of toluene. Toluene diisocyanate (TDI) in the amount of 131 grams (0.75 equivalent) was added dropwise to the flask at a uniform rate over a period of about one hour. The contents of the flask rose to 55° C., at which point cooling was applied to the flask to maintain this temperature. After all of the TDI had been added, the contents of the flask were heated to 70° C. and maintained at this temperature for 1.5 hours.

Part B

The reaction mixture of Part A was cooled to ambient temperature and 0.15 gram of p-methoxyphenol polymerization inhibitor was added. Beta-hydroxypropyl acrylate (HPA) in the amount of 98 grams (0.75 equivalent) was added to the reaction over a period of 0.5 hour. After the addition of the HPA was completed, the reaction mixture was heated to 75° C. and maintained at this temperature for six hours to complete the reaction.

The toluene solvent was removed by vacuum distillation. A clear, yellow-colored resinous product was obtained. The viscosity was 275 cps at 100° C. The infrared spectrum of the product showed no absorption at 2240 cm$^{-1}$. The absence of absorption in this region indicates that all of the isocyanate groups had reacted.

EXAMPLE 2

A product similar to that described in Example 1 was prepared in the identical manner, except that 0.75 equivalent of isophorone diisocyanate was employed in lieu of the toluene diisocyanate. The product was light yellow in color and its infrared spectrum showed no absorption characteristic of isocyanate groups.

EXAMPLE 3

Several photopolymerizable coating compositions were prepared to contain the acrylate monomers prepared in Example 1. The formulations are shown in Table I.

TABLE I

| Composition | A | B |
|---|---|---|
| Component | | |
| Proprietary Resin A (1) | 31 | 31 |
| IBA (2) | 31 | 31 |
| Monomer of Example 1 | 31 | — |
| Monomer of Example 2 | — | 31 |
| Photoinitiator (3) | 8 | 8 |

(1) Resin containing 0.375 equivalents of acrylic acid per 100 grams of resin and prepared by reacting acrylic acid with an epoxidized soybean oil.
(2) Isobornyl acrylate
(3) Mixture of equal parts of benzophenone and methyl diethanolamine Both compositions were coated onto Leneta charts to provide cast films 0.5 and 1.0 mil thick. The coatings were cured at line speeds of 20 and 100 ft/min at a power density of 200 watts/inch. All of the films were tack-free to the touch. Data on the film properties are shown in Table II.

TABLE II

| Composition | Film Thickness Mils | Line Speed ft/min | Film Hardness (1) | Film Quality (2) | Film Cure, Acetone Rubs |
|---|---|---|---|---|---|
| A | 1.0 | 100 | Soft | PM | 10 |
| " | 0.5 | 100 | Medium-Soft | FM | 3 |
| " | 1.0 | 20 | Hard | GM | 45 |
| " | 0.5 | 20 | " | GM | 35 |
| B | 1.0 | 100 | Soft | PM | 10 |
| " | 0.5 | 100 | " | PM | 10 |
| " | 1.0 | 20 | " | PM | 35 |
| " | 0.5 | 20 | Hard | GM | 25 |

(1) Estimate made by pencil test
(2) Finger nail mar test in which
PM = Poor Mar Resistance
FM = Fair Mar Resistance
GM = Good Mar Resistance

EXAMPLE 4

Photopolymerizable coating compositions containing the acrylate monomer of Example 1 were prepared. The compositions are shown in Table III.

TABLE III

| Composition | A | B | C | D |
|---|---|---|---|---|
| Component | | | | |
| Proprietary Resin A (1) | 31 | 31 | — | — |
| Proprietary Resin B (2) | — | — | 31 | 31 |
| HDDA (3) | 31 | — | 31 | — |
| TMPTA (4) | — | 31 | — | 31 |
| Monomer of Example 1 | 31 | 31 | 31 | 31 |
| Photoinitiator (5) | 8 | 8 | 8 | 8 |

(1) See footnote 1 of Table I.
(2) Resin containing 0.18 equivalents of acrylic acid per 100 grams of resin and being an acrylate-terminated urethane prepolymer.
(3) Hexanediol-1,6-diacrylate.
(4) Trimethylolpropane triacrylate.
(5) See footnote 3 of Table I.

The compositions were evaluated in the same manner as described in Example 3. All of the films were tack-free to the touch. Data on the film properties are shown in Table IV.

TABLE IV

| Composition | Film Thickness Mils | Line Speed ft/min | Film Hardness (1) | Film Quality (2) | Film Cure, Acetone Rubs |
|---|---|---|---|---|---|
| A | 1.0 | 100 | Soft | GM | 36 |
| " | 0.5 | 100 | Hard | GM | 17 |
| " | 1.0 | 20 | " | GM | 50+ |
| " | 0.5 | 20 | " | GM | 50+ |
| B | 1.0 | 100 | Med. Hard | GM | 50+ |
| " | 0.5 | 100 | Soft | GM | 16 |
| " | 1.0 | 20 | Very Hard | GM | 50+ |
| " | 0.5 | 20 | " | GM | 50+ |
| C | 1.0 | 100 | Soft | FM | 27 |
| " | 1.0 | 20 | Med. Hard | GM | 25 |
| " | 0.5 | 20 | Hard | GM | 50+ |
| D | 1.0 | 100 | " | GM | 46 |
| " | 0.5 | 100 | " | GM | 22 |
| " | 1.0 | 20 | " | GM | 50+ |
| " | 0.5 | 20 | " | GM | 50+ |

(1) See footnote (1) of Table II.
(2) See footnote (2) of Table II.

EXAMPLE 5

A series of anaerobic adhesive formulations were prepared employing the acrylate monomer of Example 2 and having the formulations shown in Table V.

TABLE V

| Composition | A | B | C | D |
|---|---|---|---|---|
| Component | | | | |
| VTBN (1) | 15 | 15 | 10 | 5 |
| TEGMA (2) | 10 | 10 | 10 | 10 |
| Monomer of Example 2 | 5 | 5 | 10 | 15 |
| t-BHP (3) | 0.75 | 1.5 | 0.75 | 0.75 |
| DMT (4) | 0.25 | 0.25 | 0.25 | 0.25 |

(1) Vinyl terminated butadiene polymer.
(2) Tetraethylene glycol dimethacrylate.
(3) t-butyl hydroperoxide.
(4) Dimethyl toluidine.

All of the compositions were employed to bond thin sheets of steel together at an applied rate of about 1 lb. of adhesive/1,000 ft² of glue line. Laps shear tensile values were obtained on specimens cured for 24 hours at room temperature. Similar values were measured on specimens cured for 2 hours at 250° F. The data are set forth in Table VI.

TABLE VI

| | Bond Strength, psi | |
|---|---|---|
| Sample | Room Temperature Cured Sample | Samples Cured 2 Hours @ 250° F. |
| A | 270 | 800 |
| B | 420 | 820 |
| C | 375 | 1490 |
| D | 760 | 1560 |

What is claimed:

1. A copolymerizable acrylate monomer useful as a component of U.V. curable resin compositions and anaerobic adhesive compositions which has the structure:

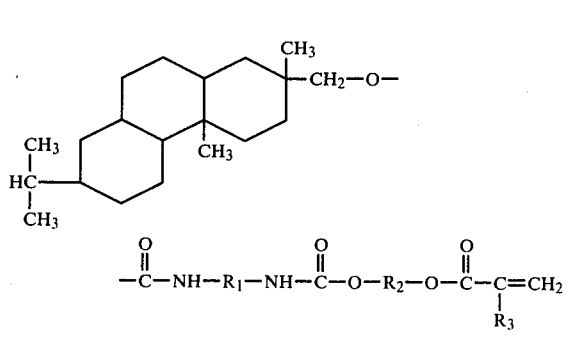

where the phenanthrene ring contains up to three (3) double bonds, where $R_1$ is a divalent isophorone alkylene or arylene radical, where $R_2$ is a divalent alkylene radical, or a divalent radical having the structure:

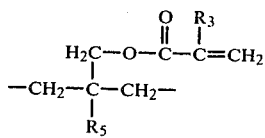

or a divalent radical having the structure:

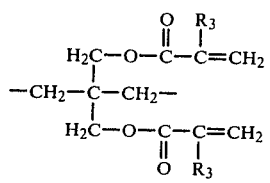

where $R_3$ is hydrogen or a methyl group and where $R_5$ is an alkyl group.

2. An acrylate monomer of claim 1 in which $R_1$ is an arylene group.

3. An acrylate monomer of claim 2 in which $R_1$ is a tolylene group.

4. An acrylate monomer of claim 1 in which $R_1$ is a hexamethylene group.

5. An acrylate monomer of claim 1 in which $R_1$ is the residue of isophorone diisocyanate.

6. An acrylate monomer of claim 1 in which $R_2$ has the structure:

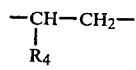

where $R_4$ is a hydrogen atom or an alkyl group.

7. An acrylate monomer of claim 1 in which $R_2$ has the structure:

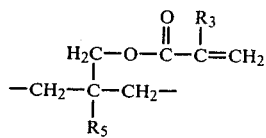

where $R_3$ is a hydrogen atom or an alkyl group and $R_5$ is an alkyl group.

8. An acrylate monomer of claim 1 in which $R_2$ has the structure:

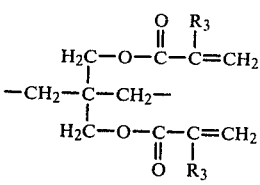

where $R_3$ is hydrogen or an alkyl group.

9. An acrylate monomer of claim 1 in which $R_1$ is a tolylene group, $R_2$ has the structure:

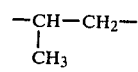

and $R_3$ is hydrogen.

10. An acrylate monomer of claim 1 in which $R_1$ is the residue of isophorone diisocyanate, $R_2$ has the structure:

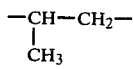

and $R_3$ is hydrogen.

* * * * *